(12) United States Patent
Paley

(10) Patent No.: US 8,450,498 B2
(45) Date of Patent: May 28, 2013

(54) IONIC LIQUID EPOXY RESIN MONOMERS

(75) Inventor: Mark S. Paley, Huntsville, AL (US)

(73) Assignee: AZ Technology, Inc., Huntsville, AL (US)

( * ) Notice: Subject to any disclaimer, the term of this patent is extended or adjusted under 35 U.S.C. 154(b) by 0 days.

(21) Appl. No.: 13/107,904

(22) Filed: May 14, 2011

(65) Prior Publication Data

US 2011/0257409 A1 Oct. 20, 2011

Related U.S. Application Data

(62) Division of application No. 12/168,085, filed on Jul. 4, 2008, now Pat. No. 8,193,280.

(51) Int. Cl.
*C07D 235/04* (2006.01)
*C07D 233/00* (2006.01)
*C07D 303/02* (2006.01)

(52) U.S. Cl.
USPC ............... 548/304.7; 548/311.1; 549/512

(58) Field of Classification Search
USPC .................. 548/304.7, 311.1; 549/512
See application file for complete search history.

(56) References Cited

U.S. PATENT DOCUMENTS

| 4,209,608 | A |   | 6/1980  | Bateman        |       |
|-----------|---|---|---------|----------------|-------|
| 4,468,228 | A | * | 8/1984  | Dvorsky et al. | 8/188 |
| 4,749,729 | A |   | 6/1988  | Kohli et al.   |       |
| 4,814,414 | A |   | 3/1989  | Newman-Evans   |       |
| 5,420,312 | A |   | 5/1995  | Andrews et al. |       |
| 5,908,943 | A |   | 6/1999  | Au et al.      |       |
| 6,140,405 | A |   | 10/2000 | Eckstein et al. |      |
| 2007/0194275 | A1 | | 8/2007 | Masuda et al.  |       |

FOREIGN PATENT DOCUMENTS

JP 02-36125 * 8/1990

* cited by examiner

*Primary Examiner* — Joseph Kosack
(74) *Attorney, Agent, or Firm* — Tomas Friend

(57) ABSTRACT

Ionic liquid epoxide monomers capable of reacting with cross-linking agents to form polymers with high tensile and adhesive strengths. Ionic liquid epoxide monomers comprising at least one bis(glycidyl) N-substituted nitrogen heterocyclic cation are made from nitrogen heterocycles corresponding to the bis(glycidyl) N-substituted nitrogen heterocyclic cations by a method involving a non-nucleophilic anion, an alkali metal cation, epichlorohydrin, and a strong base.

8 Claims, 5 Drawing Sheets

(V)

(VI)

(VII)

(XI)

(XII)

(XIII)

IONIC LIQUID EPOXY RESIN MONOMERS

CROSS-REFERENCE TO RELATED APPLICATIONS

This Application is a Division of and claims priority under 35 U.S.C. 121 to U.S. Ser. No. 12/168,085, filed Jul. 7, 2008, which is incorporated by reference in its entirety.

STATEMENT REGARDING FEDERALLY SPONSORED RESEARCH

The U.S. Government may have certain rights to this invention pursuant to NASA MSFC IRAD Project #6-04.

BACKGROUND OF THE INVENTION

The present invention relates to ionic liquid epoxide compositions and their synthesis, and to ionic liquid epoxide monomers that form polymeric resins having desirable properties as adhesives, coatings, and composites.

Fabrication and repair operations inside spacecraft and other confined spaces require composites and adhesives that produce minimal or no harmful off-gassing products. Spacecraft additionally require structural components that must be prepared in and/or withstand harsh environments such as extreme temperatures, and hard vacuum.

Current epoxies, while significantly improved over earlier materials, tend to have off-gassing and flammability issues, especially in confined environments. Many cannot be handled in a space environment because hard vacuum and cryogenic temperatures cause them to rapidly evaporate and/or freeze. Even epoxy resins that are mixed and/or cured at ambient temperature ad pressure often do not perform well at cryogenic temperatures because they become brittle. Current aerospace epoxies have a lower service temperature limit of −45° F. as neat (unfilled) resins.

Adhesives and coatings comprising ionic liquids (ILs) that avoid the use of volatile organic compounds (VOC) as a solvent are known (US 2007/0194275 A1; US 2008/0017224 A1). Adhesives and coatings of this type having high tensile and adhesive strengths both at ambient temperatures as well as cryogenic temperatures, however, are not known. The present invention overcomes these limitations by providing IL epoxide monomers that react with cross-linking agents to form polymers exhibiting high tensile and adhesive strengths at extremely low temperatures. These properties make the polymers particularly well-suited for use in adhesives, coatings, composites, or articles of manufacture for use in harsh environments such as low temperatures and high physical stresses.

BRIEF SUMMARY OF THE INVENTION

The present invention comprises a series of ionic liquid epoxide monomers and methods for their making.

DETAILED DESCRIPTION OF THE INVENTION

Figure 1:
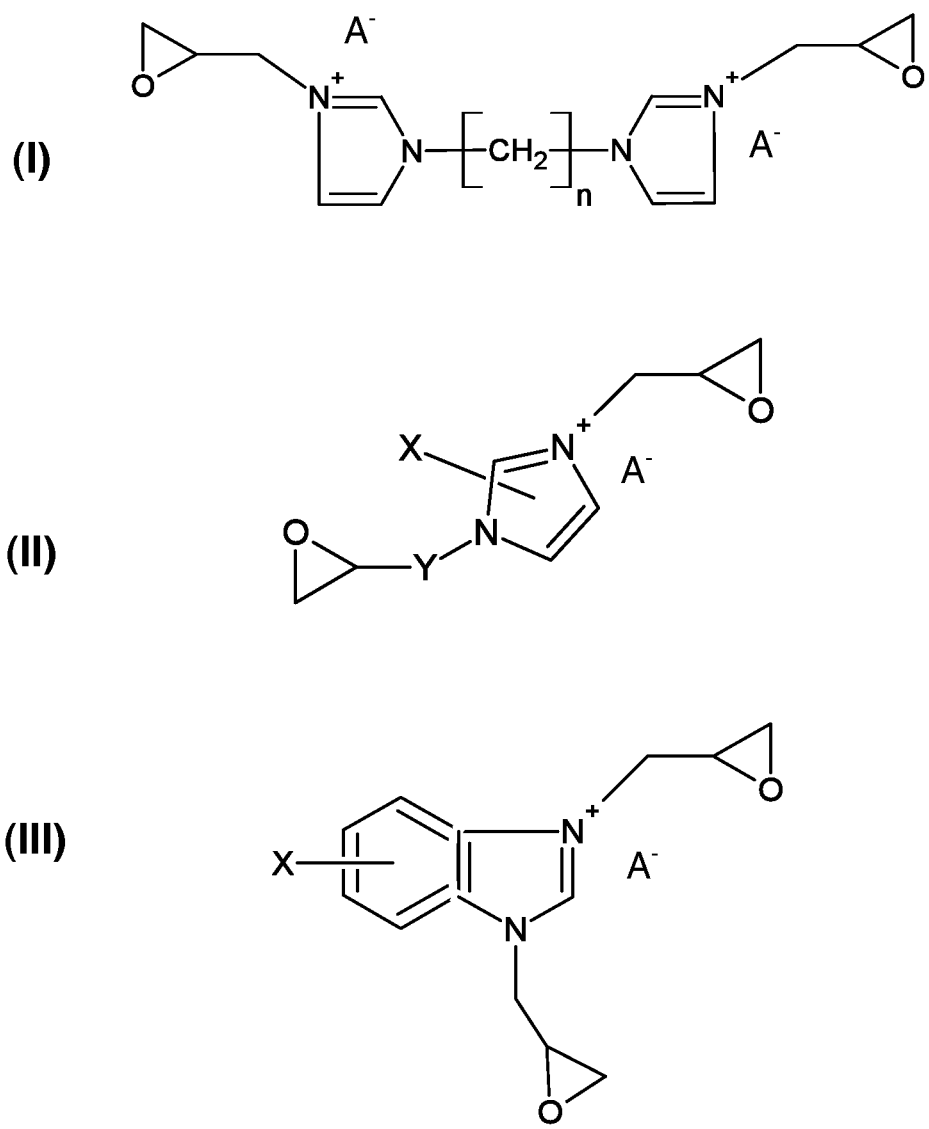
FIG. 1 shows the chemical structures of three embodiments (I-III) of ionic liquid epoxy monomer resins according to the present invention.
Figure 2:
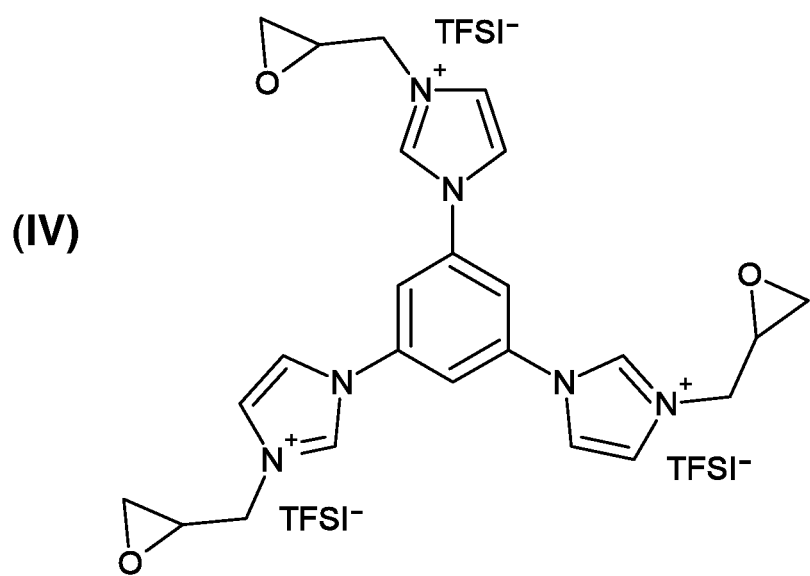
FIG. 2 shows the chemical structure of a fourth embodiment (IV) a monomer resin according to the present invention.

FIG. 1 shows the structures of three embodiments (I-III) of monomer resins according to the present invention. In the figure, X represents hydrogen, an alkyl group, a substituted alkyl group, a halogen, an aromatic ring, or a substituted aromatic group. Y represents an alkyl group, a substituted alkyl group, an aromatic ring, or a substituted aromatic group. $A^-$ represents an anion. Representative anions include $PF_6^-$, $BF_4^-$, $CF_3COO^-$, $NO_3^-$, $SO_4^{-2}$, $Cl^-$, $Br^-$, and $I^-$ and, most preferably, $(CF_3SO_2)_2N^-$ (TFSI$^-$), and $CF_3SO_3^-$. Vinylsulfonate, styrenesulfonate, or other anions that are polymerizable by free radical means are also preferred. FIG. 2 shows the structure of a fourth embodiment (IV) a monomer resin according to the present invention.

Figure 3:
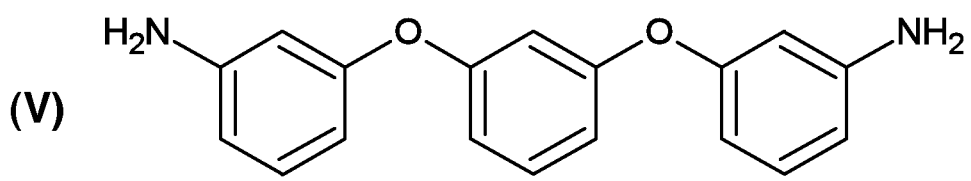
FIG. 3 shows the chemical structures of three preferred diamine curing agents (V-VII).
Figure 3:
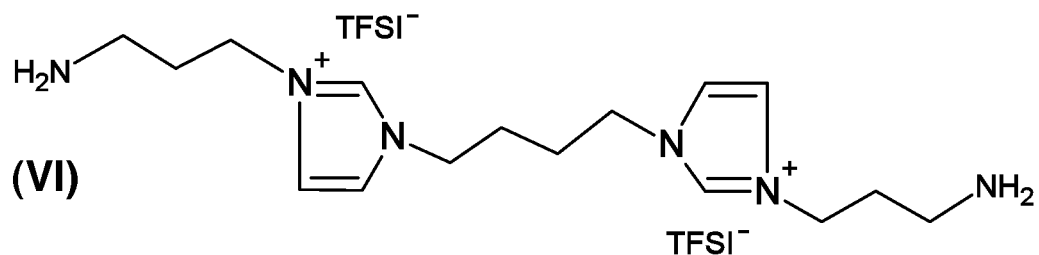
Figure 3:
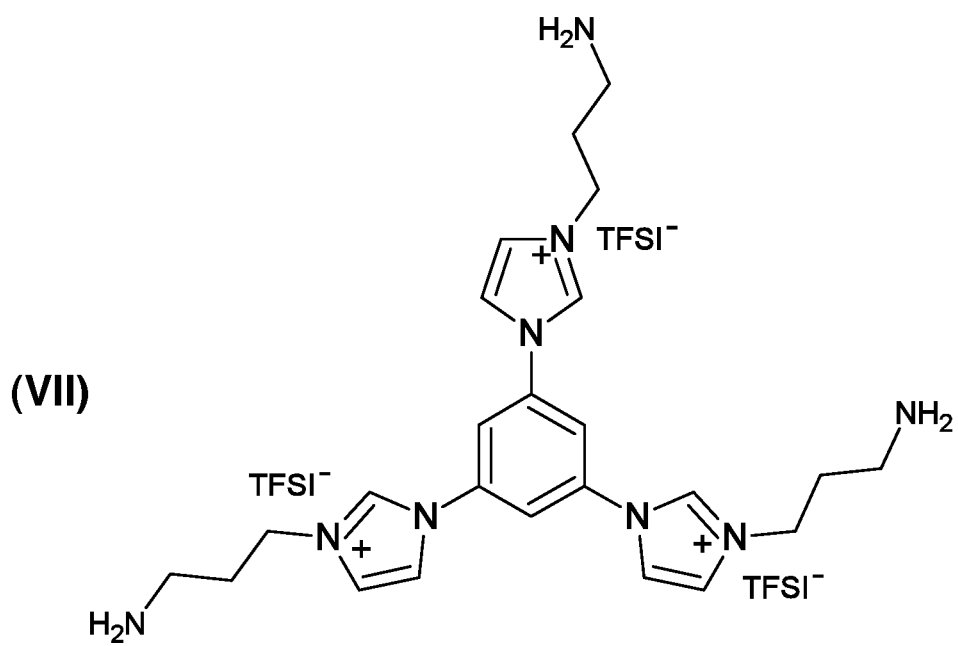

IL epoxy monomer resins are cured using curing agents such as diamine, triamine, or tetraamine compounds. A wide variety of diamines may be used as curing agents. Other agents can also be used to cure the monomer resins, including acid anhydrides, or IL-based hardening agents. FIG. 3 shows three preferred diamine/triamine curing agents (V-VII), including two IL diamines/triamines. (VI) and (VII) are IL diamines shown with TSFI$^-$ as a counter anion as an example. Anions other than TSFI$^-$ may be used.

Example 1

Synthesis of Monomer Resin (VIII)

Figure 4:
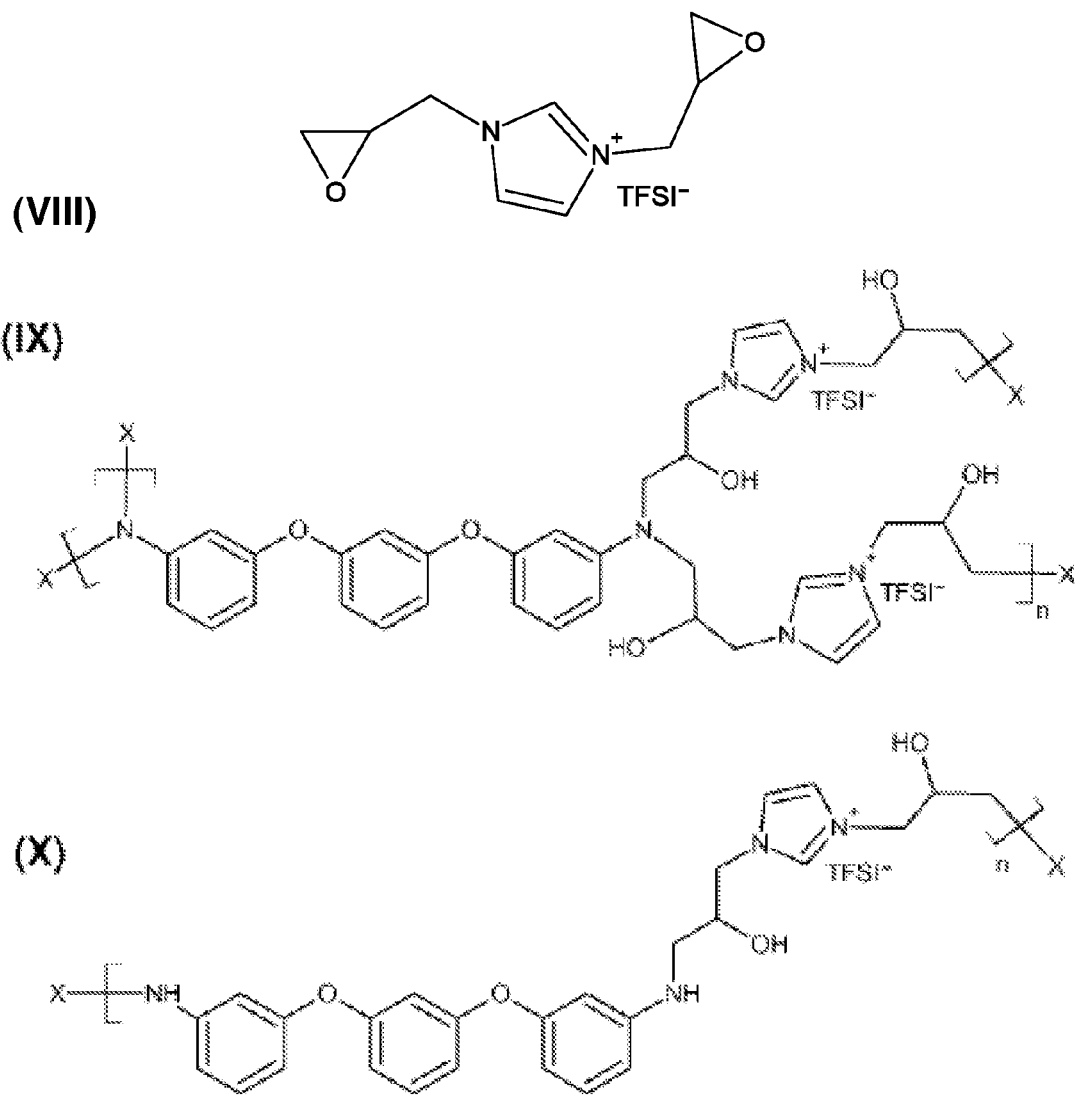
FIG. 4 shows the chemical structures of exemplary IL epoxy monomer resin (VIII), cross-linked polymeric epoxy resin (IX), and linear polymeric epoxy resin (X).

An exemplary IL epoxy monomer resin (VIII) (FIG. 4) was synthesized using the following protocol: 30 g of lithium trifluoromethanesulfonimide is added to 80 mL epichlorohydrin in a 125 mL stoppered flask surrounded by a water bath, and the mixture is stirred for several minutes until the solid dissolves completely. 6.8 g of imidazole and 4 g sodium hydroxide pellets are added and the mixture is stirred overnight, using the water bath to maintain the temperature at 20-25° C. The solid material is filtered off, and carbon dioxide gas is bubbled through the solution for 15-30 min. to neutralize residual sodium hydroxide. Excess epichlorohydrin is removed by distillation under reduced pressure, leaving a viscous liquid resin, which is then washed with 50 mL distilled water. The crude product layer is allowed to settle (15-20 min.), and the top aqueous layer is separated. The product is washed in this manner 5 or 6 times (until the wash water tests negative for chloride ion with silver nitrate solution), separated, and then dried under vacuum at 50° C. overnight, yielding approximately 30 g of 1,3-bis(glycidyl)imidazolium trifluoromethanesulfonimide, which is the IL epoxy monomer resin. The amounts of materials, temperatures, and times described are for illustrative purposes and may be modified within the scope of the present invention.

Example 2

Curing of Monomer Resin (VIII) to form Polymer Resin (IX)

To cure the ionic liquid monomer resin (VIII) into a polymeric epoxy resin, the following protocol was used: 2.5 g of the monomer resin are mixed thoroughly with 0.75 g of the aromatic diamine hardener 1,3-bis(3-aminophenoxy)benzene (APB) ((V) in FIG. 3) at 120° C. (the melting temperature of the diamine) or, alternatively, in a solution of alcohol, acetone, or other appropriate solvent. This liquid mixture is then either cast into a mold (for neat samples or composites) or applied as an adhesive/bonding agent between two surfaces within a few minutes of mixing the two components. The neat resin cures completely in 1-2 hours at 150-200° C. For mold cast samples, the curing process can be completed by heating to 200° C. for 2-4 hours, 10-12 hours at 100° C., or 70-80° C. for 24 hours to form a cross-linked polymeric epoxy resin. In the case of adhesive samples it may be advantageous to allow the mixture to set at low temperature for a few hours before curing at high temperature in order to minimize the chances of material flowing out of the adhesive joint/bondline before it has a chance to harden. The structure of the polymer formed by the reaction is represented by (IX) in FIG. 4. This ionic liquid polymeric epoxy resin has a tensile strength of 8500 psi, adhesive strengths of 5800 psi at room temperature and 6700 psi at cryogenic temperature (−196° C.), and a decomposition temperature higher than 250° C. The elastic modulus was calculated from the stress-strain data to be over 350,000 psi. The glass transition temperature is in the range 60-70° C. The amounts of materials, temperatures, and times described are for illustrative purposes and may be modified within the scope of the present invention. For example, temperatures and solvents used may be adapted according to melting temperatures and solubilities of monomers and curing agents.

Figure 5:
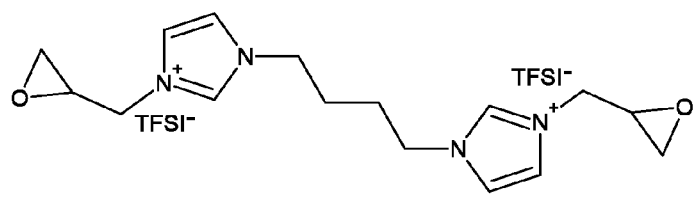
FIG. 5 shows the chemical structures of exemplary IL epoxy monomer resin (XI), cross-linked polymeric epoxy resin (XII), and linear polymeric epoxy resin (XIII).
Figure 5:
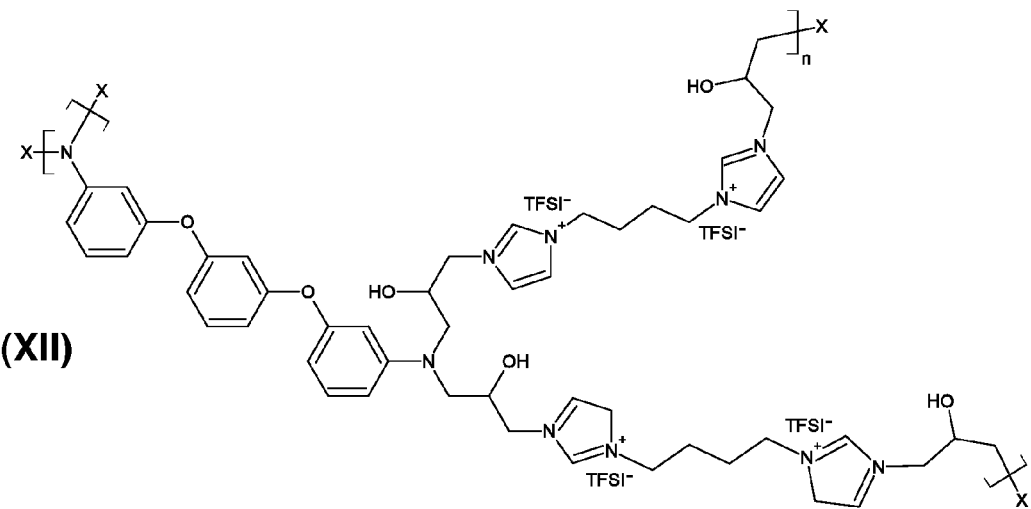
Figure 5:
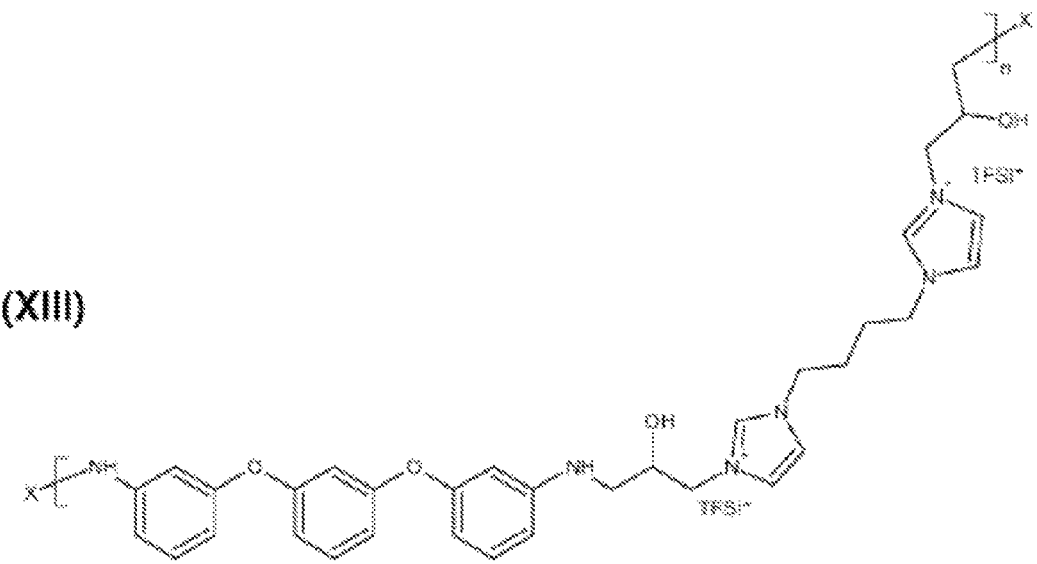

Generally, IL epoxy monomer resins comprising bis(glycidyl) N-substituted nitrogen heterocyclic cations (imidazolium, pyrrolidinium, etc.) may be synthesized by the reaction of excess epichlorohydrin with the corresponding nitrogen heterocycle. The reaction is carried out in the presence of a non-nucleophilic anion and an alkali metal cation (lithium, sodium, etc.) that can precipitate or bind to chloride ion in order to prevent ring opening and/or polymerization of the epoxide groups. A strong base such as sodium, potassium, or calcium hydroxide is also added to reverse any ring opening that does occur. Once the reaction is complete, the bis(glycidyl) substituted product is isolated from the reaction mixture and treated to remove any residual starting materials, and then, if necessary, the counter anion is exchanged by metathesis with an ionic liquid forming anion, yielding the epoxy monomer resin. Ionic liquid monomer resin (XI) shown in FIG. 5 was made in high yield using this method.

To cure an ionic liquid monomer resin into a polymeric epoxy resin, the monomer resin is mixed with a diamine hardener in a 2:1 molar ratio for diamines or divalent cross-linking agents and in a 3:1 molar ratio for triamines or trivalent cross-linking agents. This may be done at a temperature at or above the melting point of the curing agent or monomer, whichever is higher, in order to achieve a homogeneous mixture. Alternatively, the monomer and hardener (curing agent) may be mixed in a solution of alcohol, acetone, or other appropriate solvent in which both monomer and curing agent are soluble. In some cases in may be desirable to use an ionic liquid solvent. This liquid mixture may be cast into a mold (for neat samples or composites), applied as an adhesive/bonding agent between two surfaces, or applied as a coating within a few minutes of mixing the two components. For mold cast samples, the mixture is then heated to complete the curing process and form a cross-linked polymeric epoxy resin. In the case of adhesive samples it may be advantageous to allow the mixture to set at room temperature for a few hours before high temperature curing in order to minimize the chances of material flowing out of the adhesive joint/bondline. This general method was used to form polymer (XII) shown in FIG. 5 as well as its linear counterpart (XIII), which resulted from a 1:1 molar ratio of monomer resin and curing agent. When used as a component of a composite material or as a coating, other materials may be mixed with the monomer, curing agent, and/or mixture of the two prior to hardening.

In some cases it may be desirable to form IL epoxide polymers using a ration of IL epoxide monomer to curing agent that is less than 2:1. For example, compounds (V) and (VIII) may be mixed in a 1:1 molar ratio to form the polymer compound (X), or compounds (V) and (XI) may be mixed in a 1:1 molar ratio to form the polymer compound (XIII).

Heating a mixture of monomer and curing agent may be accomplished by applying a current to the mixture. The temperature and degree of curing may be varied by controlling the current applied. As the polymer forms, the conductivity of the mixture decreases, allowing the degree of polymerization to be estimated electronically during the curing process.

Example 3

Preparation of an IL Epoxide Polymer Composite

A 2-ply graphite fabric composite was prepared using a hand layup method from monomer (VIII) and curing agent (V). Testing of the resulting composite yielded an average stress at maximum load of 59,730 psi and average Modulus of $7.7 \times 10^6$ psi at room temperature. At a temperature of −150° F., the average stress at maximum load was 78,230 psi and the Modulus was $9.5 \times 10^6$ psi at −150° F. It will be understood by those skilled in the art that IL epoxide polymer composites according to the present invention may be made using materials other than graphite fabric that are commonly used in the fabrication of composite materials.

Preferred embodiments of the invention are shown and described herein. It will be clear to those skilled in the art that various changes and modifications can be made without departing from the invention as described in the following claims.

The invention claimed is:
1. An ionic liquid epoxide monomer having the general structure:

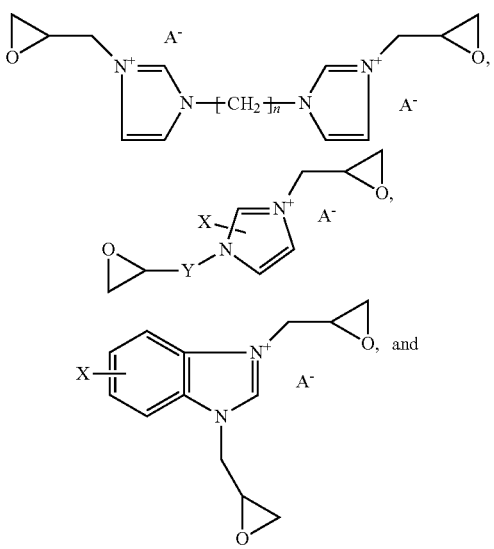

-continued

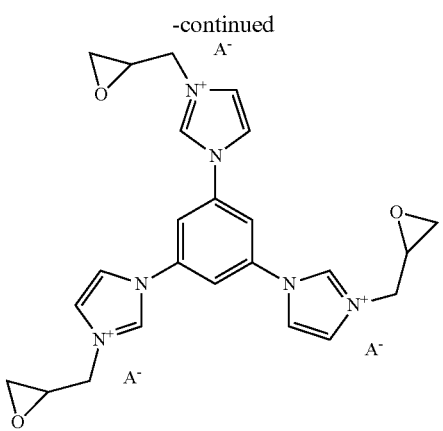

wherein: X is hydrogen, an alkyl group, a substituted alkyl group, a halogen, an aromatic ring, or a substituted aromatic group attached through a carbon atom; Y is an alkyl group, a substituted alkyl group, an aromatic ring, or a substituted aromatic group; $A^-$ is selected from the group consisting of $(CF_3SO_2)_2N^-$, $CF_3SO_3^-$, vinylsulfonate, and styrenesulfonate, and n is a positive integer.

2. The ionic liquid epoxide monomer of claim 1, having the chemical structure

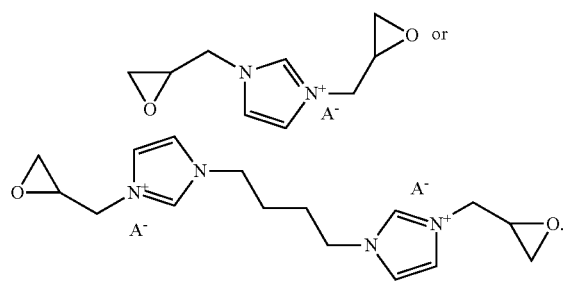

3. The ionic liquid epoxide monomer of claim 2 wherein the anion is $(CF_3SO_2)_2N^-$, or $CF_3SO_3$.

4. A method for making an ionic liquid epoxide monomer according to claim 1, comprising at least one bis(glycidyl) N-substituted nitrogen heterocyclic cation, said method comprising:
  i) dissolving a non-nucleophilic anion and an alkali metal cation in an excess epichlorohydrin to form a solution,
  ii) dissolving a strong base in the solution,
  iii) dissolving a nitrogen heterocycle corresponding to the bis(glycidyl) N-substituted nitrogen heterocyclic cation in the solution containing the strong base,
  iv) stirring the solution at a temperature of 20-25° C. for at least 2 hours, to form a precipitate,
  v) removing the precipitate from the solution,
  vi) neutralizing residual strong base,
  vii) removing excess epichlorohydrin to leave a viscous ionic liquid epoxide monomer resin
  viii) removing chloride ion by washing the ionic liquid epoxide monomer resin with water, and
  ix) removing residual water from the ionic liquid epoxide monomer resin.

5. The method of claim 4, wherein the non-nucleophilic anion is trifluoromethanesulfonimide and the alkalai metal cation is lithium cation.

6. The method of claim 4, wherein the ionic liquid epoxide monomer resin has the chemical structure

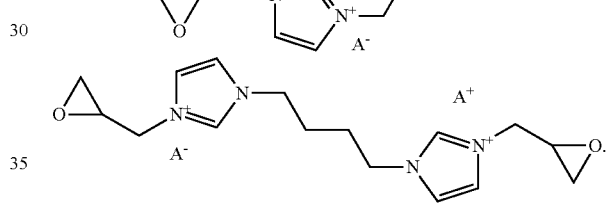

7. The method of claim 4, wherein the ionic liquid epoxide monomer resin is washed with water until the wash water tests negative for chloride ion with silver nitrate solution.

8. The method of claim 4, wherein the strong base is neutralized by bubbling carbon dioxide through the solution.

* * * * *